United States Patent
Zhokhavets et al.

(10) Patent No.: US 11,243,075 B2
(45) Date of Patent: Feb. 8, 2022

(54) SYSTEM FOR THE OPTICAL DETECTION OF OBJECTS

(71) Applicant: Phenospex B. V., Heerlen (NL)

(72) Inventors: Uladzimir Zhokhavets, Aachen (DE); Grégoire Martin Hummel, Maastricht (NL); Stefan Schwartz, Wurselen (DE)

(73) Assignee: Phenospex B.V., Heerlen (NL)

( * ) Notice: Subject to any disclaimer, the term of this patent is extended or adjusted under 35 U.S.C. 154(b) by 580 days.

(21) Appl. No.: 15/897,541

(22) Filed: Feb. 15, 2018

(65) Prior Publication Data
US 2018/0245915 A1    Aug. 30, 2018

(30) Foreign Application Priority Data
Feb. 28, 2017 (EP) ..................................... 17158455

(51) Int. Cl.
*G01C 3/08* (2006.01)
*G01B 11/25* (2006.01)
(Continued)

(52) U.S. Cl.
CPC .............. *G01C 3/08* (2013.01); *A01G 7/00* (2013.01); *G01B 11/25* (2013.01); *G01C 3/00* (2013.01); *G01N 21/255* (2013.01); *G01N 21/31* (2013.01); *G01N 33/0098* (2013.01); *G01N 21/359* (2013.01); *G01N 22/00* (2013.01);
(Continued)

(58) Field of Classification Search
CPC ... G01N 2021/1734; G01N 2021/1736; G01N 2021/1748; G01N 2021/1751; G01N 2021/1753; G01N 21/255; G01N 21/256; G01N 2021/8466; A01G 7/00; G01C 3/08
See application file for complete search history.

(56) References Cited

U.S. PATENT DOCUMENTS 6,142,629 A    11/2000  Adel et al.
9,134,593 B1   9/2015   Worley, III et al.
(Continued)

FOREIGN PATENT DOCUMENTS

DE    102005014525 A1    10/2006
EP       1607041 A2      12/2005
(Continued)

OTHER PUBLICATIONS

Busemeyer, Lucas et al., BreedVision—A Multi-Sensor Platform for Non-Destructive Field-Based Phenotyping in Plant Breeding, Sensors, Feb. 27, 2013, pp. 2830-2847, vol. 13.

*Primary Examiner* — Eric L Bolda
(74) *Attorney, Agent, or Firm* — The Webb Law Firm

(57) ABSTRACT

A system for the optical detection of objects includes a first source for generating light, microwaves, or ultrasound of a first wavelength. An object is illuminated by the light, the microwaves, or the ultrasound, wherein the illumination is distorted by the object. The system further includes at least one color light source for the generation of color light of a second wavelength, wherein the same object is illuminated by the color light of the color light source. The first wavelength is different from the second wavelength. Further, a sensor is provided for the detection of the object illuminated by the first source, and a second sensor is provided for the detection of the color light generated by the color light source, which is reflected by the object.

21 Claims, 4 Drawing Sheets

(51) Int. Cl.
*G01N 21/359* (2014.01)
*G01C 3/00* (2006.01)
*G01N 33/00* (2006.01)
*G01N 21/31* (2006.01)
*G01N 21/25* (2006.01)
*A01G 7/00* (2006.01)
*G01N 29/04* (2006.01)
*G01N 22/00* (2006.01)
*G01N 21/84* (2006.01)
*G01V 8/20* (2006.01)

(52) U.S. Cl.
CPC ..... *G01N 29/04* (2013.01); *G01N 2021/8466* (2013.01); *G01V 8/20* (2013.01)

(56) References Cited

U.S. PATENT DOCUMENTS

| | | | | |
|---|---|---|---|---|
| 2002/0008055 A1* | 1/2002 | Campbell | .............. | G01N 21/85 209/577 |
| 2003/0067613 A1* | 4/2003 | Ishikawa | .................. | G06T 7/521 356/614 |
| 2007/0002306 A1* | 1/2007 | Kalayeh | ............... | G01N 21/314 356/4.07 |
| 2009/0213362 A1* | 8/2009 | Nakamura | .............. | A61B 5/444 356/72 |
| 2010/0014096 A1* | 1/2010 | Alameh | ................ | G01N 21/255 356/484 |
| 2012/0062706 A1* | 3/2012 | Keshavmurthy | ....... | G01S 17/87 348/47 |
| 2015/0373321 A1* | 12/2015 | Bridges | ................... | G01S 17/48 348/46 |
| 2017/0358106 A1* | 12/2017 | Yoshimura | ............ | G06F 16/951 |
| 2018/0143130 A1* | 5/2018 | Shearer | ................ | A01B 79/005 |
| 2020/0084958 A1* | 3/2020 | Reusch | ................... | A01G 25/16 |

FOREIGN PATENT DOCUMENTS

| | | |
|---|---|---|
| EP | 2799848 A1 | 11/2014 |
| GB | 2427913 A | 10/2007 |

* cited by examiner

SYSTEM FOR THE OPTICAL DETECTION OF OBJECTS

CROSS-REFERENCE TO RELATED APPLICATION

This application claims priority to European Patent Application No. 17158455.0 filed Feb. 28, 2017, the disclosure of which is hereby incorporated in its entirety by reference.

BACKGROUND OF THE INVENTION

Field of the Invention

The present invention relates to a system for the optical detection of objects using laser triangulation.

Description of Related Art

It is known to optically detect objects by means of laser triangulation. In doing so, an object is illuminated using a laser. Due to the topology of the object, the illumination by the laser is distorted.

An image of the object illuminated is captured by a camera, and elevation information about the object is extracted from the distortion of the illumination. The laser triangulation exclusively provides elevation information about the topology of the object. Therefore, known laser triangulation methods and systems only offer the possibility to further characterize an object or to differentiate from other objects based on its elevation information.

In many cases objects cannot be characterized or differentiated by their elevation information alone. This is true in particular when objects are similar, but not exactly the same, such as for instance cars, animals, plants or the like.

In particular with plants, it is necessary for a characterization to be able to make a statement about the disease condition, the nutritional condition and/or the ripeness a plant's fruits. It is further necessary to be able to make a differentiation between the individual plants, e.g. in the field, so that only specific plants are detected. All this is not possible using known laser triangulation, since it only provides elevation information.

SUMMARY OF THE INVENTION

Therefore, it is an object of the present invention to provide a system for the optical detection of objects with an improved possibility of characterizing the object.

The object is achieved with a system for the optical detection of objects according to claims 1 and 2 and with the system according to claim 12.

The system of the present invention for the optical detection of objects by means of laser triangulation comprises a source for generating light, microwaves or ultrasound of a first wavelength. An object is illuminated by the light, the microwaves or the ultrasound and the illumination is distorted by the object. The system further comprises at least one color light source for the generation of color light of a second wavelength, wherein the same object is illuminated by the color light of the color light source. The first wavelength is different from the second wavelength. A first sensor captures the object illuminated by light, microwaves or ultrasound from the source. Elevation information about the object can be determined therefrom based on the distortion of the illumination. In particular, the illumination has a predefined shape such as e.g. a line or the like. The same is distorted by the topology of the object so that the distorted illumination is detected by the first sensor and elevation information can be determined from the distortion. A second sensor detects the color light generated by the color light source, which is reflected by the object. Thus, it is possible to determine color information about the object. Based on the color information it is possible to further characterize the object and, in particular, to differentiate similar objects based on different color information. If this object is, in particular, a plant, the disease condition, the nutritional condition and/or the ripeness of the plant's fruits can be determined in a simple manner based on the color information.

As an alternative, the system of the present invention for the optical detection of objects merely comprises only a first sensor for capturing the object illuminated by the light, the microwaves or the ultrasound from the source, whereby elevation information is again determined in the manner described above. At the same time, the first sensor detects the color light generated by the color light source and reflected by the object. Thereby, it is possible to calculate color information about the object. Thus, only the first sensor is used both for calculating the elevation information about the object and to calculate the color information.

Preferably, the source is a line laser. Thus, the object is illuminated by the line laser in a line by line manner, wherein the line of the line laser is distorted by the topology of the object and elevation information about the object can be determined therefrom along the line of illumination. In particular, only a single line is generated.

Preferably, the first wavelength is in the range of a band gap in the solar spectrum. Band gaps are caused by the absorption of sunlight in the atmosphere. In the range of these band gaps, no sunlight or only little sunlight reaches the surface of the earth. Since no or only little sunlight exists in the range of the band gaps, this has no or only a slightly compromising effect on capturing the object.

The first wavelength preferably is 900 nm to 1000 nm and, as is particularly preferred, is in the range between 920 nm and 960 nm. In particular, the first wavelength is 940 nm.

The second wavelength is preferably selected from the wavelength ranged of near infrared (NIR), red, green and/or blue. Here, the wavelength of the NIR is 780 nm to 3 µm, the wavelength of red is 640 nm to 780 nm, the wavelength of green is 490 nm to 570 nm, and that of blue is 430 nm to 490 nm. In particular it is possible to include other colors such as e.g. orange (600 nm to 640 nm), yellow (570 nm to 600 nm), violet (380 nm to 430 nm) and near UV (200 nm to 380 nm). This allows the calculation of specific color information about an object. In this regard, the second wavelength is in particular restricted to one of the above ranges. Thus, a single color light source only generates light of a single color. The color light source is in particular not a white light source.

Preferably, a plurality of color light sources are provided, wherein all color light sources in particular have respectively different wavelengths and the wavelengths of the color light sources are selected from NIR, red, green and/or blue. In particular, the wavelength ranges of the individual color light sources may be designed to overlap each other. As an alternative thereto, only light of a single color is generated by a single color source without overlap. Thus, the color light sources are in particular not white light sources. Due to the provision of a plurality of color light sources with different wavelengths, a more precise characterization of the object is possible, in particular since a detailed statement can be made on the present disease condition, nutritional condition and/or ripeness of a plant's fruits or, as an alternative thereto, in the characterization of and/or discrimination between similar, yet not identical objects such as e.g. cars, animals and the like.

The color light source preferably is one or a plurality of LEDs. LEDs (Light Emitting Diodes) are available at low cost in a wide emission spectrum. In particular, LEDs are bright enough and can be switched quickly, so that a quick capturing of objects is possible. For this purpose, it may be provided that exactly one LED is provided per wavelength or wavelength range or, as an alternative thereto, a plurality of LEDs may be provided per each wavelength or each wavelength range so that their lighting intensity is combined.

Preferably, the color light reflected by the object is diverted from the optical beam path of the source for generating light or ultrasound through a beam splitter towards the first or second sensor. In this regard it is evident that, if the system comprises only a first sensor, the reflected color light is directed to the first sensor via the beam splitter. As an alternative, if the system has a first and a second sensor, the reflected color light is diverted to the second sensor via a beam splitter. As an alternative or in addition to a beam splitter, a dichroic mirror may be provided to divert the reflected color light out of the optical beam path of the source for generating light or ultrasound in a wavelength-selective manner. In particular, due to the dichroic mirror which, as is particularly preferred, is tuned to be wavelength-selective for the first wavelength, the first wavelength can be reflected, whereas the second wavelengths are transmitted. The reversed situation is also possible, so that the first wavelength is transmitted, whereas all second wavelengths are reflected.

Preferably, the first or the second sensor only detects the color light when a color light source is active. In this regard it is self-evident that, if the system only comprises a first sensor which also detects the reflected color light, the first sensor only detects the color light when a color light source is active. If the system has a first and a second sensor, the second sensor only detects the reflected color light when a color light source is active. In addition, the first sensor only detects the light or the ultrasound when the source is active. Thus, the only the reflected color light is detected when a color light source is actually active. An inadvertent influence of color light or light and ultrasound on each other is prevented thereby. In particular when a plurality of color light sources is provided, all color light sources are successively activated, the reflected light is detected and the respective color light source is deactivated before another color light source is activated. A mutual influence of the color light sources on each other is reduced thereby. It is possible to obtain and to subsequently evaluate the color information of the object independently for each wavelength or for each wavelength range of a color light source. No mixing of all of the color information occurs in the process. If, for example, a statement can be made on the nutritional condition of the plant based on the reflected green color light, this is not possible if, e.g. the object is illuminated with red color light at the same time.

Preferably, the color light and the light, the microwaves or the ultrasound of the source are directed towards the object at least in part along the same optical path and are directed in particular on the same point of the object. As an alternative or in addition thereto, the color light and the light microwaves or the ultrasound of the source may be directed towards the object at least in part in a common plane. In particular, the color light sources can be provided on both sides next to the source for generating light, microwaves or ultrasound and emit into the same direction. Here, the color light and the light, the microwaves or the ultrasound of the source are directed towards the object throughout the entire optical path and in particular in a common plane. As an alternative thereto, one or a plurality of color light sources may e.g. be arranged on one side or on both sides next to a deflection mirror for the light microwaves or the ultrasound. Here, the optical path of the color light and the light or the ultrasound, starting from the deflection mirror, is at least partially the same or is in a common plane. It is ensured thereby that no offset occurs on the object between the light, the microwaves or the ultrasound and the color light, which offset could lead to errors in the detection by the first and/or the second sensor. In particular, it is possible to always obtain a sharp image of the illuminated region of the object by the first and/or second sensor. In addition, due to this arrangement, the distance between the color light source and the object is clearly known. Thereby, it is possible in particular to perform a correction on the intensity of the reflected color light that specifically takes this distance into account. Here, it may be taken into account that farther points on the object reflect a lower intensity of the color light back to the first or second sensor than nearer points on the object.

Preferably, the system is movable and/or the object is movable, whereby the system can be moved relative to the object in order to capture the entire object. A relative movement between the system and the object is performed so as to successively capture all parts of the object. In this respect, it is possible in particular to perform either a continuous movement of the system and the object relative to each other or a step-wise movement after each detection of light or ultrasound and/or color light.

The first sensor and/or the second sensor preferably are CCD sensors. The system preferably comprises mirrors for the deflection of the color light and or the light or the ultrasound. Preferably the first sensor and/or the second sensor are adapted to acquire the light intensity of the reflected light.

The system preferably comprises lenses for reproducing the illuminated object onto the first sensor and/or second sensor.

The system preferably comprises filters for wavelength selection, which in particular are a bandpass filter in front of the first sensor, which only allows the passage of the wavelength of the light, the microwave or the ultrasound in the case that the system comprises a first and a second sensor. In this case, a further filter for wavelength selection can be provided in front of the second sensor, which is also configured as a bandpass, which only allows wavelengths of the color light to pass.

The object preferably is a plant, in particular a harvest product, an animal, a car or the like.

The invention further relates to a method for the optical detection of an object by means of laser triangulation, wherein a source for generating light, microwaves or ultrasound of a first wavelength is activated to illuminate the object, wherein the illumination is distorted by the object, whereafter an image is captured and elevation information about the object is determined from the distortion of the illumination. After the image has been captured, the source for generating light or ultrasound is deactivated. Thereafter, a color light source for generating color light of a second wavelength is activated, wherein the object is illuminated by the color light of the color light source. Then, an image is captured for detecting the reflected color light, wherein color information about the object is determined from the reflected color light. Thereafter, the color light source is deactivated. In this case, according to the invention, the first wavelength is different from the second wavelength, wherein the second wavelength is selected from NIR, rot, green, yellow or blue. The method is not restricted to the exact sequence of steps, so that in particular interchanging of the detection of elevation information and color information is also encompassed.

Preferably, an image is captured as a reference image without the source for generating light, microwaves or ultrasound, as well as the color light source being activated. Thereby, the background illumination is determined, which can then be considered in the evaluation for calculating the elevation information or for calculating the color information.

Preferably, a plurality of color light sources, in particular for NIR, red, green and blue, are activated in succession and a respective image is captured. Thus, successively, a color light source is activated, an image is captured and the source is deactivated again.

Preferably, for a complete capturing of the object, the method steps are repeated several times as a cycle, wherein in particular the source for generating light or ultrasound and/or the color light source are moved relative to the object so as to capture all of the object. For this purpose, the object can be moved or the source for generating light or ultrasound and/or the color light source can be moved. Accordingly, a cycle comprises the determination of the elevation information as described above and, thereafter, the consecutive determination of all color information. Here, the sequence can of course be selected freely. In particular, at least one reference image is generated in each cycle. By the relative movement of between the object and the source or the color light source, it is possible to capture the entire object. In this regard, such a relative movement may be performed stepwise after each cycle or continuously.

Preferably, a plurality of images are captured for one color during a cycle. In particular the intensity of the color light in the individual images of a color is different. For example, a first image is captured with the full intensity of the color light source for the respective color, and then a second image is captured for the same color with a lower intensity of the color light source. Thus, it is possible to increase the contrast, in particular by overlaying the images of a corresponding color. In this manner, a High Dynamic Range (HDR) image can be obtained for each of the colors.

Preferably, the method is further developed according to the features of the system for the optical detection of objects as described above and in particular according to claims 1 to 11.

BRIEF DESCRIPTION OF THE DRAWINGS

The invention will be described hereunder in more detail with reference to a preferred embodiment and to the accompanying drawings.

In The Figures.

DESCRIPTION OF THE INVENTION

Figure 1:
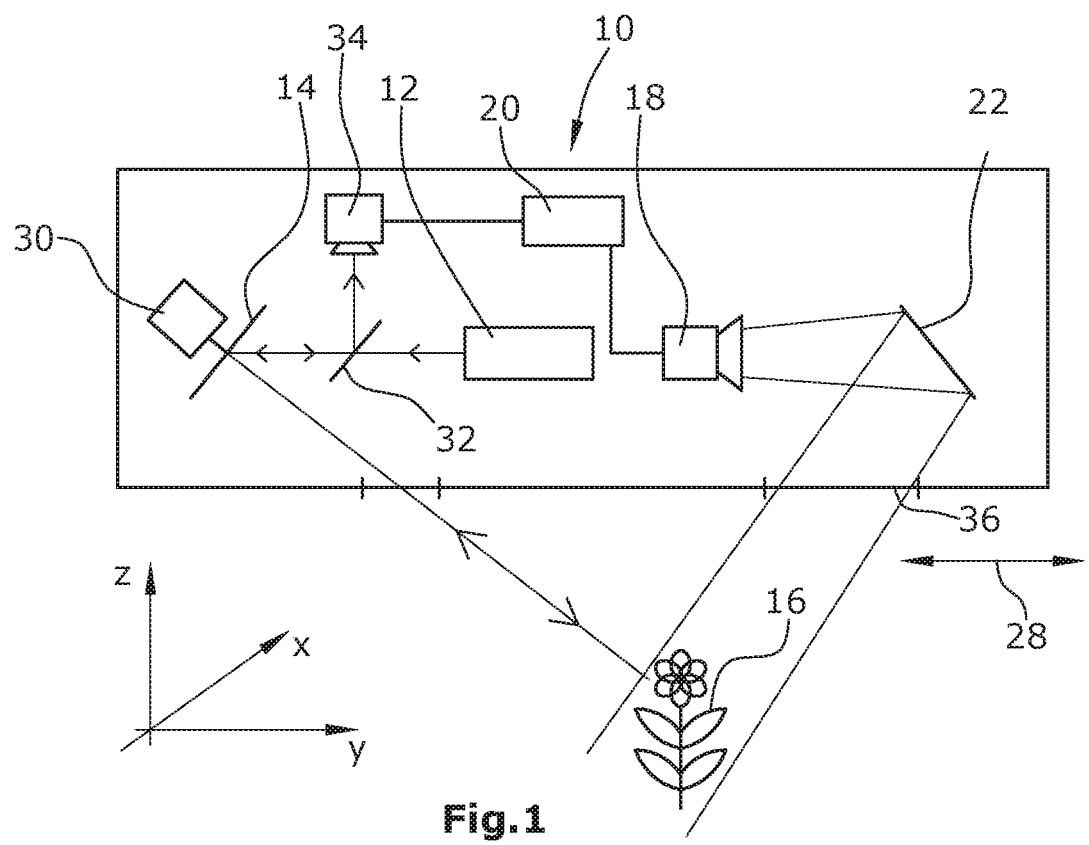
FIG. 1 shows an embodiment of the system for the optical detection of objects according to the present invention.
Figure 3:
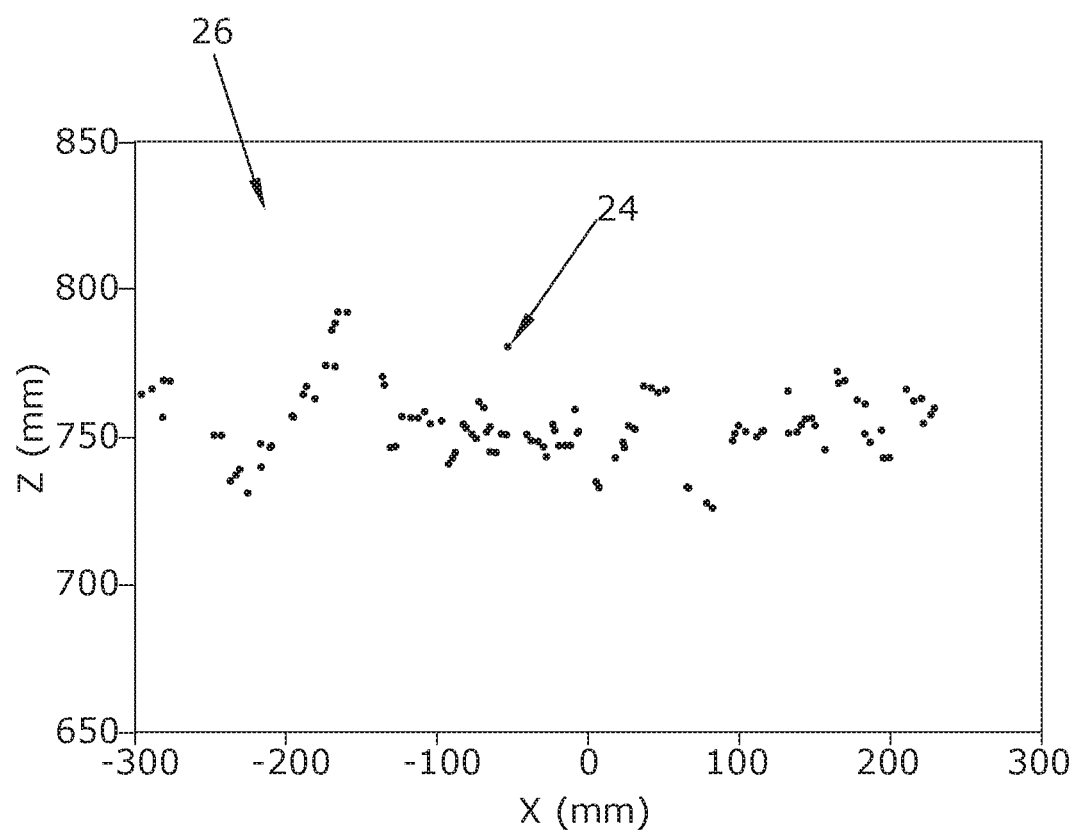
FIG. 3 shows an elevation profile captured by the system for the optical detection of objects illustrated in FIG. 1.

The laser triangulation system of the present invention for the optical detection of objects as illustrated in FIG. 1 comprises a housing 10. A source 12 for generating light is arranged inside the housing 10, which source may be e.g. a line laser. The light of the line laser 12 illuminates an object 16, illustrated as a plant, via a mirror 14. The topology of the plant 16 causes a distortion of the line-shaped illumination of the line laser 12. The object 16, and in particular the distorted line-shaped illumination of the object 16, is detected by a first sensor 18 via a mirror 22, wherein the sensor is also arranged inside the housing 10. The first sensor 18 is connected to an evaluation unit 20, wherein elevation information about the object along the line-shaped illumination can be determined by the evaluation means based on the distortion of the line-shaped illumination caused by the object 16. A typical elevation profile is shown in FIG. 3. A plurality of data points 24 are determined along the line of the line laser 12, which together form an elevation profile 26. Here, the entire housing 10 of the system can be moved along the arrows 28 in the y-direction so that the entire topology of the object 16 can be captured successively by means of a plurality of elevation profiles 26.

In addition the system comprises a plurality of color light sources 30 configured as LEDs and adapted to generate red, green, blue and near infrared light. The object 16 is illuminated by the color light sources 30. Here, the illumination by the color light sources 30 occurs in a plane identical to the illumination by the line laser 12. In FIG. 1 the common plane is perpendicular to the y/z-plane. The color light reflected by the object 16 reaches a second sensor 34 via the mirror 14 and a dichroic mirror 32. The dichroic mirror 32 transmits light of the wavelength of the line laser 12 and reflects all other wavelengths. The second sensor 34 captures the reflected color light, and the evaluation unit 20 calculates color information about the object.

The first sensor 18 and the second sensor 34 are designed as CCD cameras, for example in order to acquire the light intensity in particular independently of the respective wavelength.

For preventing the first sensor 18 from being affected by sunlight, the housing 10 comprises a filter input 36 configured as a bandpass and exclusively transmitting light of the wavelength of the line laser 12. The wavelength of the line laser 12 is selected in particular to correspond to a band gap in the solar spectrum so that there is only little or no influence by sunlight.

Figure 2:
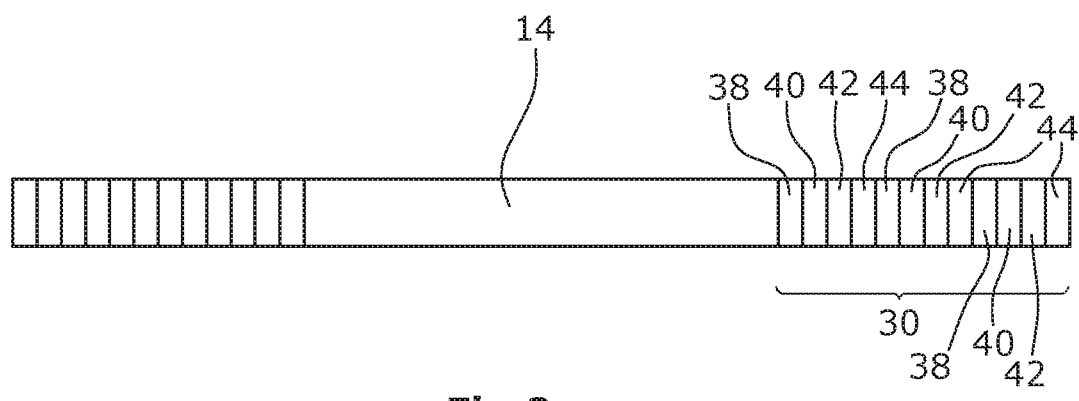
FIG. 2 shows a detail of the system for the optical detection of objects illustrated in FIG. 1.

The color light sources 30 are arranged on both sides next to the mirror 14 (as illustrated in FIG. 2). A first color light source formed by three red light LEDs 38 on the one side and another three red light LEDs on the other side are arranged alternating with green light LEDs 40, blue light LEDs 42 and LEDs 44 for generating near-infrared light. Here, the arrangement on the left and on the right of the mirror 14 is in particular symmetric.

Figure 4:
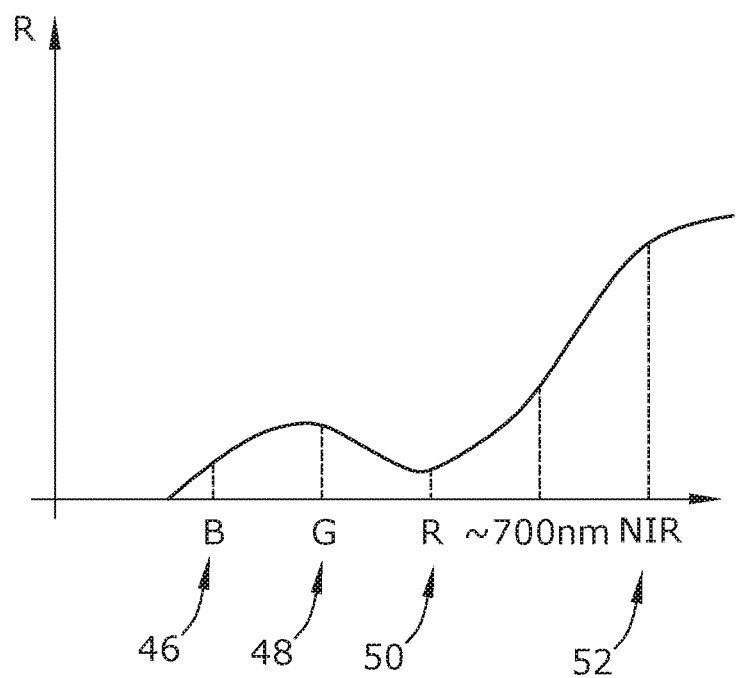
FIG. 4 shows a characteristic reflection spectrum of a plant.

Based on the color information obtained by means of the color light source 30 and the second sensor 34, it is possible to perform an exact characterization of the object 16 and to differentiate similar, yet not exactly identical objects 16 from each other. If the object is e.g. a plant, it is possible to determine the nutritional condition of the plant based on the color information and/or to determine diseases or the disease condition the plant. Further, the ripeness of a plant's fruits can be determined based on the color information. In particular, the color information provides a possibility to differentiate, whether the object is actually a plant. In this regard, FIG. 4 illustrates a characteristic reflection spectrum of a plant having a low proportion of blue 46, a high proportion of green 48, a low proportion of red 50 and a characteristic steep rise in the near infrared 52. It is possible to determine from the color information, in particular from the difference between the red range 50 and the near infrared range 52, whether the object is actually a plant or another not vegetal object.

Figure 5:
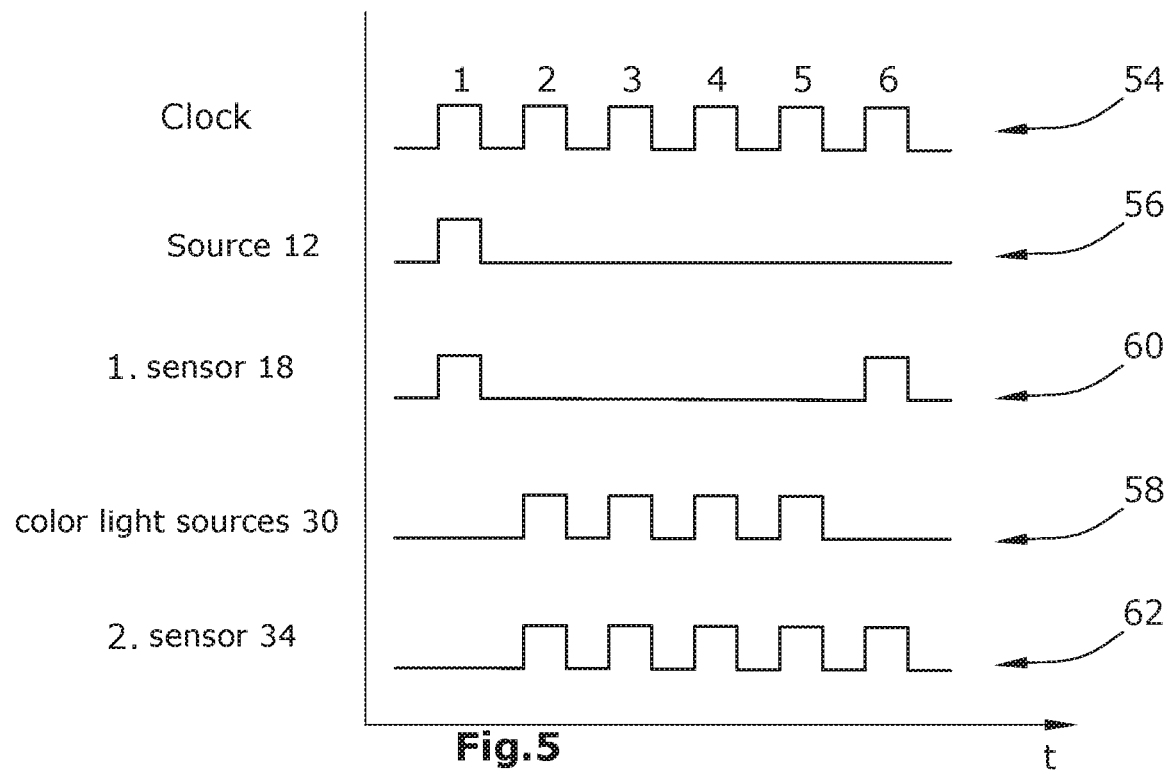
FIG. 5 shows a flow chart of the method for the detection of an object according to the present invention.

FIG. 5 illustrates a cycle of the method according to the invention for the optical detection of objects. The cycle comprises six pulses. Each pulse has a length of 0.05 to 1 µs. The frequency of the cycles is 10 to 500 Hz. The first line 54 illustrates the clock of a cycle generated by a pulse generator. The second line 56 illustrates the activation of the line laser 12. The same is activated at the first pulse. At the same time, according to the second line 56, an image is captured by the first sensor 18. The second sensor 34 does not capture an image at the first pulse. The color light sources 30 remain deactivated as well. From the second to the fifth pulse all color light sources are activated one after the other and, at the same time, an image is captured by the second sensor 34, as indicated in the third and the fourth line 58, 62 in FIG. 5. For example, the red light LED 38 is activated at the second pulse, the green light LED 40 is activated at the third pulse, the blue light LED 42 is activated at the fourth pulse and the near infrared LED 44 is activated at the fifth pulse. The color information can be determined from these images by the evaluation unit 20. At the sixth pulse, neither the color light source nor the line laser 12 is activated, and the first sensor 18 and the second sensor 34 capture an image as a reference image.

The system is displaced relative to the object 16 as indicated by the arrows 28, either after a full cycle has been passed or continuously. In this manner the system is captured in its entirety. In particular, the complete color information about the object 16 is obtained to enable an exact characterization of the object 16.

Figure 6:
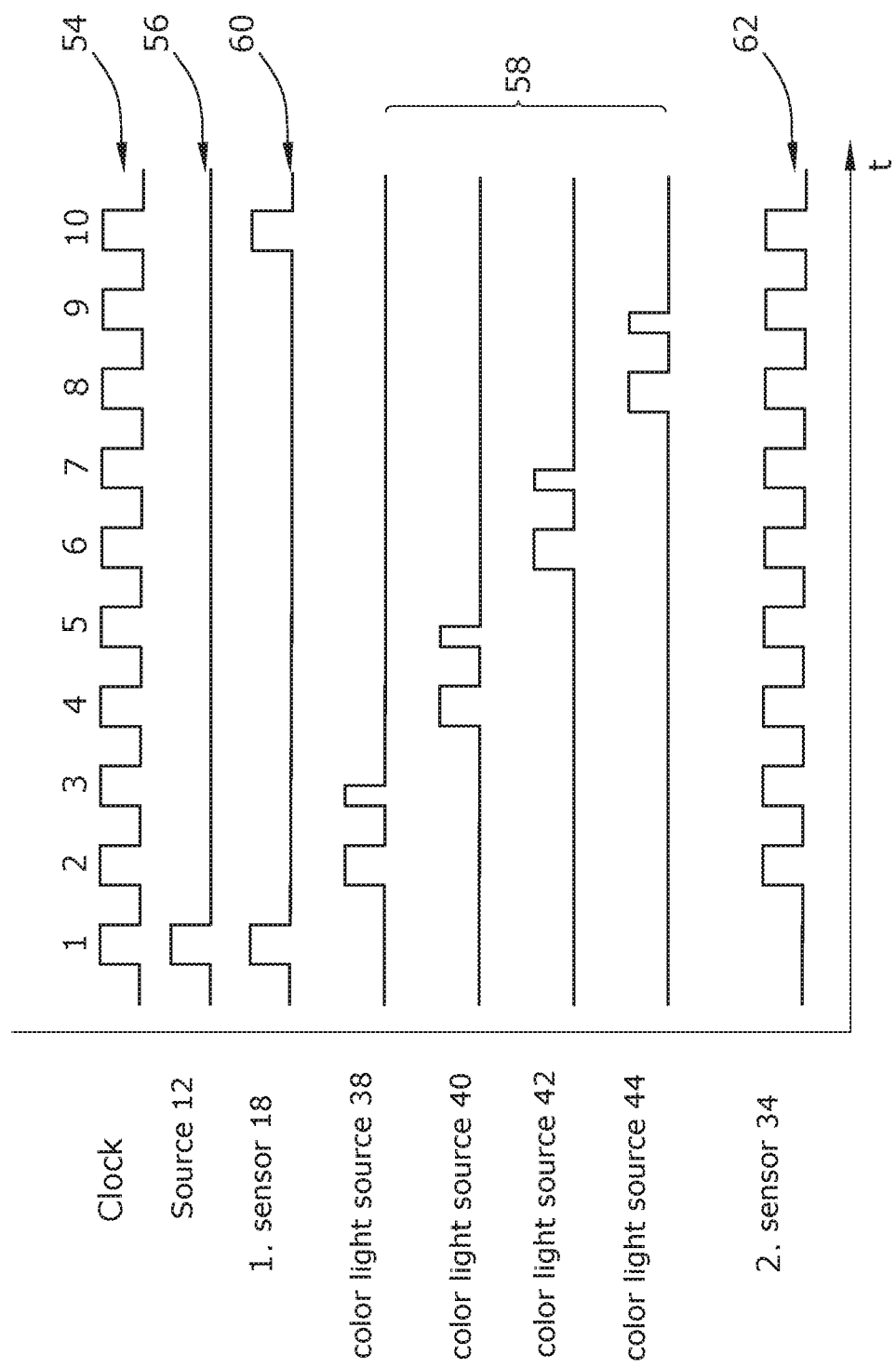
FIG. 6 shows a flow chart of another method for the detection of an object according to the present invention.

FIG. 6 illustrates a cycle of another method of the present invention for the optical detection of objects. Here, two images are captured for each color, i.e. each color light source 38, 40, 42, 44 is activated twice in one cycle. The second sensor 34 is activated accordingly. Here, first, an image is captured for each color with the full intensity of the color light, and thereafter, by a shortened activation, an image with a lower intensity of the color light is captured upon the second activation of the color light source 38, 40, 42, 44. This is illustrated in the corresponding lines in FIG. 6. The further proceeding of the method corresponds to the method in FIG. 5.

The invention claimed is:

1. A system for the optical detection of objects using laser triangulation, comprising:
   a line laser for generating light of a first wavelength;
   a dichroic mirror in a first optical path between the line laser and an object;
   a first mirror in the first optical path to reflect the light to illuminate the object, wherein the illumination is distorted by the object;
   at least one color light source for generating color light of a second wavelength, the at least one color light source arranged next to the first mirror, wherein the object is illuminated by and reflects the color light of the at least one color light source to the first mirror, and the first mirror reflects the color light of the at least one color light source to the dichroic mirror,
   wherein the first wavelength is different from the second wavelength and the dichroic mirror diverts the color light of the at least one color light source out of the first optical path;
   a second mirror in a second optical path between the object and a first sensor for detecting the object illuminated by the light of the line laser, wherein the second mirror reflects the light of the line laser to the first sensor and the light of the line laser is detected only by the first sensor; and
   a second sensor for detecting the color light generated by the at least one color light source and reflected by the object to the first mirror and the dichroic mirror, wherein the color light generated by the at least one color light source is detected only by the second sensor.

2. A system for the optical detection of objects using laser triangulation, comprising:
   a line laser for generating light of a first wavelength, wherein an object is illuminated by the light and the illumination is distorted by the object when the line laser is activated;
   a plurality of color light sources for generating color light of a plurality of second wavelengths, wherein all of the plurality of color light sources have different second wavelengths, respectively, wherein the object is illuminated by each respective color light source of the plurality of color light sources when the respective color light source is activated,
   wherein the first wavelength is different from the plurality of second wavelengths;
   a first sensor for detecting the object illuminated by the light of the line laser when the line laser is activated and for detecting the color light generated by the plurality of color light sources and reflected by the object when each respective color light source is activated,
   wherein the line laser is activated to capture a first image of the light distorted by the object and then deactivated, and
   wherein, after deactivation of the line laser, each respective color light source of the plurality of color light sources is activated in succession to capture a respective image of the color light reflected by the object and then deactivated.

3. The system of claim 1, wherein the at least one color light source is one or a plurality of LEDs.

4. The system of claim 1, wherein the first wavelength is in a range of a band gap in a solar spectrum.

5. The system of claim 1, wherein the second wavelength is selected from NIR, red, green, and blue.

6. The system of claim 1, wherein the at least one color light source is a plurality of color light sources, and all color light sources have different wavelengths, respectively, and each wavelength of all color light sources is selected from NIR, red, green, and blue.

7. The system of claim 1, wherein the reflected color light is diverted from the first optical path of the line laser by the dichroic mirror to the second sensor.

8. The system of claim 1, wherein the second sensor only detects the reflected color light when a color light source of the at least one color light source is activated, and the first sensor only detects the light of the line laser when the line laser is activated.

9. The system of claim 1, wherein the color light of the at least one color light source and the light of the line laser are directed to the object at least partly along the first optical path.

10. The system of claim 1, wherein the system is moved relative to the object to detect all of the object, wherein the system is movable and/or the object is movable.

11. A method for the optical detection of an object using laser triangulation, comprising:
   a. activating a line laser for generating light of a first wavelength to transmit to a dichroic mirror in a first optical path between the line laser and an object and to reflect from a first mirror in the first optical path to illuminate the object, wherein the illumination is distorted by the object, and wherein the light reflects from a second mirror in a second optical path between the object and a first sensor;
   b. capturing an image with the first sensor and determining elevation information about the object from the distortion;
   c. deactivating the line laser for generating the light;
   d. activating a plurality of color light sources for generating color light of a plurality of second wavelengths, wherein all of the plurality of color light sources have different second wavelengths, respectively, wherein the plurality of color light sources are arranged next to the first mirror, wherein the object is illuminated by and reflects the color light of the plurality of color light sources to the first mirror, the first mirror reflects the color light of the plurality of color light sources to the dichroic mirror, and the dichroic mirror diverts the color light of the plurality of color light sources out of the first optical path to a second sensor;
   e. capturing an image of the reflected color light with the second sensor and determining color information about the object from the reflected color light; and
   f. deactivating the plurality of color light sources, wherein the first wavelength is different from the plurality of second wavelengths, and the plurality of second wavelengths are selected from NIR, red, green, yellow, and blue.

12. The method of claim 11, further comprising capturing a reference image without the line laser for generating the light and the plurality of color light sources being activated.

13. The method of claim 11, the method further comprising activating the plurality of color light sources and capturing one image.

14. The method of claim 11, further comprising repeating all steps several times as a cycle for a complete detection of the object, wherein the line laser for generating the light and/or the plurality of color light sources are moved relative to the object to detect the object in its entirety.

15. The method of claim 11, wherein an intensity of the color light is variable and, within a cycle comprising a repetition of the steps of the method a plurality of times, a first image is captured with color light of a defined wavelength and a second image is captured with color light of a same wavelength, wherein the intensity of the color light differs for the first image and the second image.

16. The system of claim 4, wherein the first wavelength is in a range from 900 nm to 1000 nm.

17. The system of claim 16, wherein the first wavelength is in a range from 930 nm to 960 nm.

18. The system of claim 17, wherein the first wavelength is 940 nm.

19. The system of claim 4, further comprising a filter input between the object and the second mirror along the second optical path, the filter input configured as a bandpass to transmit the light of the first wavelength and to reflect all other wavelengths in the solar spectrum.

20. The system of claim 1, wherein the dichroic mirror is configured to transmit the light of the first wavelength and to reflect all other wavelengths.

21. The system of claim 1, wherein the dichroic mirror is configured to reflect the light of the first wavelength and to transmit all other wavelengths.

* * * * *